(12) United States Patent
Bosco et al.

(10) Patent No.: US 8,530,450 B2
(45) Date of Patent: Sep. 10, 2013

(54) MIXED BUTYRIC-FORMIC ESTERS OF ACID POLYSACCHARIDES, AND THEIR PREPARATION AND USE AS SKIN COSMETICS

(75) Inventors: Marco Bosco, Gradisca d'Isonzo (IT); Luca Stucchi, Pavia di Udine (IT); Rita Gianni, Monrupino (IT); Antonia Trevisan, Trieste (IT)

(73) Assignee: Sigea S.R.L., Trieste (IT)

( * ) Notice: Subject to any disclaimer, the term of this patent is extended or adjusted under 35 U.S.C. 154(b) by 550 days.

(21) Appl. No.: 12/744,738

(22) PCT Filed: Nov. 20, 2008

(86) PCT No.: PCT/EP2008/009801
§ 371 (c)(1),
(2), (4) Date: Jun. 7, 2010

(87) PCT Pub. No.: WO2009/068215
PCT Pub. Date: Jun. 4, 2009

(65) Prior Publication Data
US 2010/0305061 A1  Dec. 2, 2010

(30) Foreign Application Priority Data

Nov. 27, 2007  (IT) .............................. MI2007A2237

(51) Int. Cl.
*A61K 31/70* (2006.01)
*A61K 31/715* (2006.01)
*C08B 37/00* (2006.01)
*C07H 5/04* (2006.01)
*C07H 5/06* (2006.01)
*C07H 1/00* (2006.01)

(52) U.S. Cl.
USPC ................ 514/62; 514/54; 536/53; 536/55.2; 536/55.3; 536/124

(58) Field of Classification Search
USPC ..................... 514/62, 54; 536/53, 55.2, 55.3, 536/124
See application file for complete search history.

(56) References Cited

U.S. PATENT DOCUMENTS
2,589,226 A  3/1952  Carson

FOREIGN PATENT DOCUMENTS

| | | |
|---|---|---|
| EP | 1 942 117 | 7/2008 |
| GB | 487 020 | 6/1938 |
| WO | 03/008457 | 1/2003 |
| WO | 2005/054297 | 6/2005 |
| WO | WO 2005092929 A1 * | 10/2005 |
| WO | 2008/081255 | 7/2008 |

* cited by examiner

*Primary Examiner* — Patrick Lewis
*Assistant Examiner* — Everett White
(74) *Attorney, Agent, or Firm* — Lucas & Mercanti, LLP

(57) ABSTRACT

Disclosed are acid polysaccharides characterized by the concomitant presence of alcohol groups esterified with butyric and formic acids.

21 Claims, 1 Drawing Sheet

HA: Commercial sample Mw = 300 kDa

● : HABF example 4: D.S. = 0.7 (butyric), 0.04 (formic)

▲ : HABF example 2: D.S. = 0.2 (butyric), 0.07 (formic)

MIXED BUTYRIC-FORMIC ESTERS OF ACID POLYSACCHARIDES, AND THEIR PREPARATION AND USE AS SKIN COSMETICS

This application is a U.S. national stage of PCT/EP2008/009801 filed on Nov. 20, 2008, which claims priority to and the benefit of Italian Application No. MI2007A002237 filed on Nov. 27, 2007, the contents of which are incorporated herein by reference.

The present invention discloses mixed butyric-formic esters of acid polysaccharides and their preparation by a process wherein the formate ester originates from formamide in the presence of butyric anhydride and bases, their purification and recovery by dialysis and freeze-drying, and their use as elasticising and moisturising substances for cosmetic and skin protection use.

STATE OF THE ART

In view of their chemico-physical and biological characteristics, glycosaminoglycans (GAGs) are products of great interest in the application field due to the crucial role they play in particular areas of the human body, where they are generally present in the form of proteoglycans. Said molecules are complex systems wherein the polysaccharide chains may be bonded covalently or non-covalently to proteins. They perform multiple biological functions, ranging from regulation of the water in the tissues, as ion diffusion modulators in extracellular matrix, to regulation of cell motility and other functions, from involvement in the reproductive system to acting as a mere supporting framework.

The GAG which has been most studied and subjected to chemical modifications is hyaluronic acid (HA).

In general, the modifications to HA relate to the use of new derivatives, mainly in the biomedical sector, such as biomaterials, controlled drug release, viscosupplementation products, post-surgical anti-adhesion devices, etc. In cosmetics, HA is mainly used as a moisturiser in unmodified native form characterised by specific molecular weights.

According to the literature, the greatest efforts have recently focused on processes of crosslinking HA to obtain new biocompatible molecules with particular biological characteristics (viscoelasticity); for example, EP 341745 describes products obtained by autocrosslinking of HA for use in intra-articular treatment, by viscosupplementation, and also as post-surgical antiadhesion devices.

Other patents, such as U.S. Pat. Nos. 4,582,865 and 4,713,488, claim said properties, using exogenous molecules as crosslinking agents.

Ester derivatives with carboxyl are described in EP 216453 for the use of modified HA in the field of biomaterials and controlled drug release.

There are far fewer patents relating to hydroxyl esters of HA with organic acids. For example, U.S. Pat. No. 5,679,657 claims an HA acetylate with a degree of substitution of between 0.6 and 3.6, starting from HA with low viscosity and low molecular weight, for cosmetic use as a filming agent; U.S. Pat. No. 6,017,901 claims the use of hemisuccinate ester derivatives of HA to introduce further negative charges into the polysaccharide chain.

EP 941253 discloses the synthesis of HA derivatives with butyric anhydride in a basic environment, to obtain products esterified at the level of the hydroxyl functions.

No functionalisations of other GAGs for uses in the dermatological/cosmetic field are known as far as we are aware. The simultaneous presence of butyrate and formate residues as a result of the original synthesis process used and claimed is not described in any of the cases mentioned.

DESCRIPTION OF THE INVENTION

The present invention relates to acid polysaccharide derivatives partly or totally esterified with butyric and formic acids at the free hydroxyl groups of acid polysaccharides belonging to the glycosaminoglycan (GAG) family, in particular hyaluronic acid, chondroitin sulphate, dermatan sulphate, heparan sulphate and keratan sulphate. The invention relates to the process for the preparation thereof.

The products according to the invention are useful in topical (cosmetic or medical) preparations which possess moisturising, elasticising, skin-toning, anti-aging and anti-acne activity, and as adjuvants in the treatment of skin lesions such as inflammations, ulcers, and hyperthermia lesions induced by radiation such as UV, X and gamma rays.

The degree of substitution (DS) of the hydroxyl groups of each polysaccharide monomer can vary, in the case of butyric esters between 0.01 and 1*N, preferably between 0.01 and 0.2*N, where N is the number of free alcohol groups present in the repetitive unit, while the degree of esterification of formic acid on the hydroxyl groups of the polymer is between 0.01 and 0.2 (namely between 1% and 20%).

The degree of esterification, which is modulatable and reproducible, can vary, and depends on the characteristics of the starting polysaccharide and the reaction conditions used, such as the stoichiometric ratios between the polysaccharide substrate, the type of catalytic base used, and the butyric anhydride.

Any carboxyl functions not esterified can be present in acid form or salified with alkali metals, especially sodium.

The molecular weight of acid polysaccharides is usually between $10^3$ and $10^7$ daltons; if the polysaccharide is hyaluronic acid, the molecular weight is preferably between $10^4$ and $10^6$ daltons.

In the case of hyaluronic acid, the degree of esterification of butyric acid on the hydroxyl groups of the polymer is preferably between 0.01 and 0.8, whereas the degree of esterification of formic acid on the hydroxyl groups of the polymer is between 0.01 and 0.20.

By varying the degree of esterification of the individual components, the chemico-physical and rheological characteristics of the derivatives according to the invention vary, and they can be used in topical compositions for treatment as moisturising, elasticising, skin-toning, anti-aging or anti-acne agents or as adjuvants for the treatment of skin lesions, such as inflammations, ulcers, wounds, dermatitis, and skin hyperthermia caused by irradiation.

The invention also relates to the method of preparing said derivatives.

Said process involves:

a) dissolving the acid polysaccharide, salified with sodium or other alkali metals, in formamide by heating, at temperatures of between 60° C. and 120° C., and preferably 95° C.;

b) adding butyric anhydride to the resulting solution, at room temperature, in the presence of an organic base;

c) diluting the homogenous, viscous reaction mixture with an aqueous solution of NaCl and neutralising it to pH 6-7.5;

d) purifying the dilute reaction mixture by dialysis or tangential filtration;

e) freezing the purified polysaccharide solution and recovering the product by freeze-drying or spray-drying.

The organic base is an aromatic or aliphatic base including at least one atom of trisubstituted nitrogen, preferably dimethylaminopyridine or triethylamine.

One of the advantages of the compounds according to the invention compared, for example, with native (unmodified) commercial hyaluronic acid is that the presence of the butyric and formic ester substituents of the modified polymer protects against enzymatic degradation by the hyaluronidases present in the tissues. Said novel property of the compounds according to the invention is illustrated by the following experiment.

Commercial HA sodium salt and the samples obtained as described in examples 2 and 4 are used in the experiment.

The mother solution of polysaccharide (10 mg/ml) is left under gentle mechanical stirring for one hour at 37° C. before addition of the enzyme. Starting with said solution, 10 ml of a dilute solution (1 mg/ml) containing 0.1 mg/ml of the enzyme (bovine testicular hyaluronidase 1060 U/mg) is prepared. A second dilute solution is prepared with a dose of enzyme ten times lower. Both solutions are left to incubate at 37° C. 0.6 ml samples are taken at regular intervals and placed in a water bath at 100° C. for 5 mins., filtered to eliminate the enzyme, and then frozen.

Determination of Distribution of Mean Weighted Molecular Weight by HP-SEC-TDA Chromatography The samples were subjected to size-exclusion chromatography using a combination of four detectors (light scattering at 90° and 8°, refraction index and viscometer). Processing of the chromatogram allows the distribution of molecular weights Mw (ponderal molecular weight) to be determined.

Chromatography Conditions

Instrumentation: Viscotek pump, model VE1121; in-line two-channel degasser, Gastorr 150.

Columns: 2×GMPWXL mixed-bed columns, 7.8 mm ID×30 cm, Viscotek; temperature 40° C.

Mobile phase: 0.1 M $NaNO_3$.

Flow rate: 0.6 ml/min.

Detector: Viscotek mod. 302 TDA equipped with refraction index, capillary viscometer and light scattering with measurement at 90° and 8°, and temperature of 40° C.

Volume injected: 100 µl.

Figure 1:
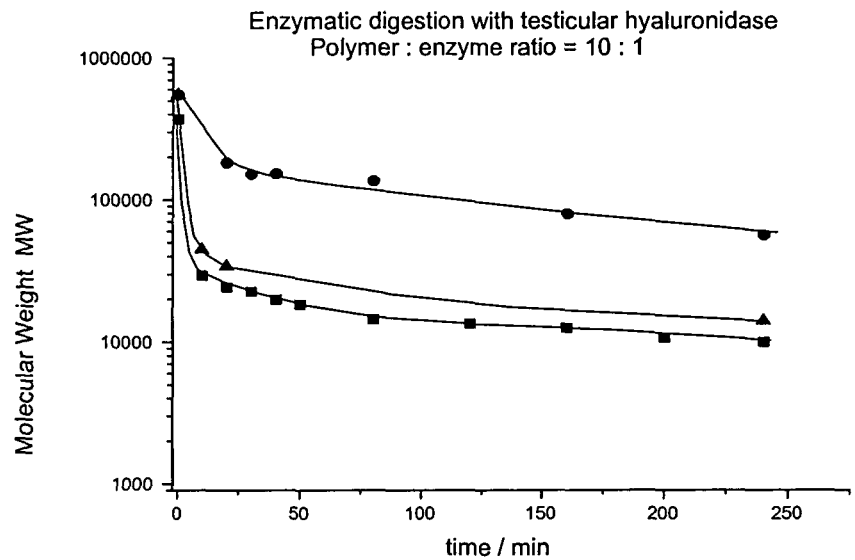
FIGS. 1 and 2 show the values of molecular weight Mw relating to the samples taken from the polymer solutions incubated with the enzyme in the 0-4 hour interval. The samples containing native-non-substituted hyaluronic acid presented a faster rate of breakdown than those partly esterified with butyric/formic acid according to the invention. The degree of depolymerisation reached at the plateau is also greater for the native polymer. Both effects are modulated by the degree of substitution in butyrate/formate esters.
Figure 2:
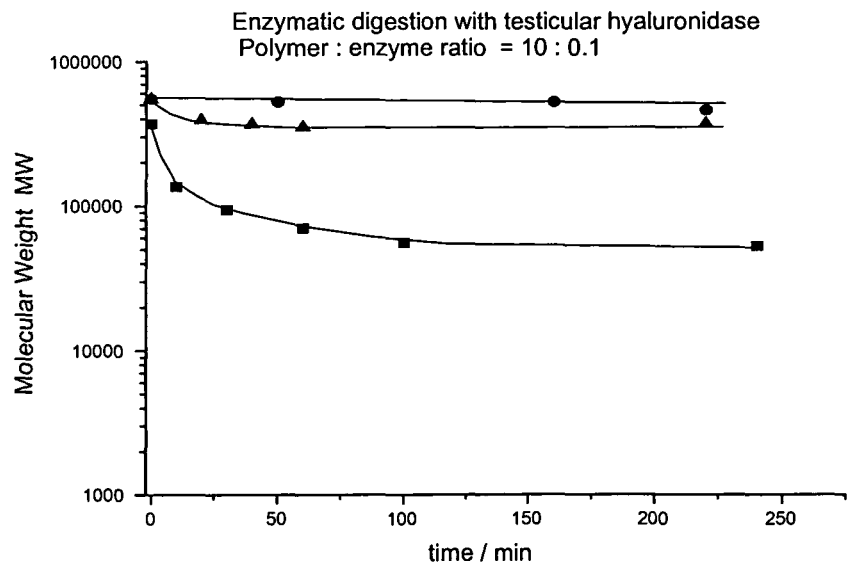

With a polymer:enzyme ratio of 10:1 (FIG. 1), the compound relating to example 4 with a high degree of esterification maintains a polymerisation rate at the end of the experiment (4 hours) about ten times greater than that of the native polymer. With a polymer:enzyme ratio of 100:1 (FIG. 2), the compounds according to the invention are not depolymerised at all, whereas the molecular weight of native HA is reduced by around two-thirds.

Evaluation of Efficacy In Vivo on Healthy Volunteers

The acid polysaccharide esters according to the invention demonstrated powerful elasticising activity in experiments conducted in vivo on healthy volunteers.

An example that illustrates the invention is set out below.

A gel was prepared containing 0.1% of mixed butyrate/formate ester of HA sodium salt obtained as described in example 2, in deionised water (98.35%), together with excipients, namely a thickener (0.5%), and preservatives (1.05%).

A gel with the same composition, containing commercial HA sodium salt at the same concentration (0.1%) and with the same excipients, was used as comparator.

The purpose of the experiment was to evaluate the efficacy of a gel formulation containing a compound according to the invention (treatment group A), by comparison with unmodified commercial HA sodium salt, (treatment group B), with instrumental measurements of moisturisation and elasticity.

24 volunteers (mean age 49.8 years) applied each product to half the face twice a day, every day, for four weeks.

At the start of the test period (To) and at the end of the four weeks' treatment (Tf), instrumental measurements of skin moisturisation and elasticity in the periocular area were performed at the application sites. The volunteers completely removed the product by washing with water three hours before the instrumental recordings.

The level of moisturisation of the stratum corneum of the face was measured with a corneometer, an instrument that measures the level of moisturisation of the skin surface, while skin elasticity was measured by the elastometric suction method using a cutometer, an instrument that measures the deformation of the skin surface when it is sucked into a measuring probe. A constant negative pressure of 350 mbars was created for one second inside the probe in contact with the skin. The experiment consisted of three suction/release cycles which measured the deformation of the elastic characteristics of the skin, indicated as parameter R2.

The results thus obtained are summarised in the table below:

| | \multicolumn{5}{c}{Determination of biological elasticity (Parameter R2)} | | | | |
|---|---|---|---|---|---|
| | To | Tf | Variation | % Variation | t-test (To-Tf) |
| Group A | 0.460 | 0.574 | 0.114 | 24.8 | $P < 0.001$ |
| Group B | 0.511 | 0.523 | 0.012 | 2.3 | $p > 0.05$ |

The data shown in the table indicate that for the preparation obtained according to the invention (Group A) there was a highly significant increase in parameter R2 (biological elasticity), while the comparison product (Group B) did not present any significant effect on parameter R2.

As regards the moisturisation parameter, there was no significant difference between times To and Tf for either treatment group; this result is explained by the type of experimental protocol used, which scheduled the washing out of the preparation three hours before the instrumental measurements.

Evaluation of Soothing Action on Skin Subjected to Heat Stress by Radiation

Eight patients suffering from breast cancer, with a mean age of 52 years, were treated by radiotherapy with a linear accelerator of gamma particles.

The treatment cycle comprised 15 treatments, involving the administration of 2 Gy fractions, five days a week, making a total administered dose of 30 Gy.

The purpose of the study was to evaluate the possibility of performing all the required treatment cycles, the tolerability of the product, and its protective efficacy.

The ointment obtained as described in example 9 was applied to the irradiated area every day, three times a day, at intervals of 8 hours between applications, always starting 2 hours before the radiotherapy treatment and continuing for 5 days after completion of the radiotherapy. The irradiated skin area was evaluated at this stage.

All patients tolerated the planned treatment cycle (30 Gy), demonstrating the excellent protective effect and tolerability of the preparation used.

The efficacy of the treatment was also assessed by scoring the adverse reactions on the irradiated skin. Specifically, the following scores were assigned:

0: no reaction
1: slight erythema
2: moderate erythema
3: severe erythema
4: desquamation.

One patient of the 8 presented desquamation, 1 moderate erythema, 1 slight erythema, and 5 no reaction.

In conclusion, this preliminary trial with a cream preparation according to the invention demonstrated good tolerability and an excellent local protective effect against radiotherapy-induced dermatitis.

These findings clearly indicate that the derivatives according to the invention can be advantageously used as active ingredients of topical compositions mixed with dermatologically acceptable inert carriers.

The derivatives according to the invention could be present in percentages ranging between 0.05% and 5% by weight. Suitable compositions include creams, ointments, gels, hydrophilic liquids, aqueous or water-alcohol lotions, oil/water or water/oil emulsions.

The preparation of mixed butyric/formic esters of acid polysaccharides is reported in the following examples.

EXAMPLE 1

Synthesis of Butyric and Formic Ester of Hyaluronic Acid Sodium Salt (BUT07005)

5.00 g of sodium hyaluronate with a molecular weight of approx. 300 kDa is solubilised in 100 mL of formamide at 95° C., under nitrogen flow and with mechanical stirring for approx. 1 hour.

The resulting polysaccharide solution is left to cool at room temperature, and 503.3 mg of a solution of 4-dimethylaminopyridine in 5 mL of formamide is dropped, at the rate of 1.67 mL/min. After 15 minutes, 734 µl of butyric anhydride is added and left to react for 40 minutes. The reaction mixture, which is homogenous and highly viscous, is transferred to 1.2 L of 0.9% NaCl (w/v).

The solution is filtered under reduced pressure through a sintered glass filter, and then further diluted with a 0.9% NaCl solution (w/v) to the final volume of 2.5 L.

The product is purified by tangential filtration through a filter membrane with a porosity of 10 kDa, first against 0.9% NaCl (w/v), and then exhaustively against ultra-pure water.

Finally, the solution is frozen, and the product is recovered by freeze-drying; 4.03 g of white lyophilisate is obtained. The lyophilisate is analysed by $^1$H NMR.

Degree of substitution of butyric ester (DS but.): 0.13, degree of substitution of formic ester (DSform.): 0.07.

EXAMPLE 2

Synthesis of Butyric and Formic Ester of Hyaluronic Acid Sodium Salt (BUT07002)

5.00 g of sodium hyaluronate with a molecular weight of approx. 300 kDa is solubilised in 100 mL of formamide at 95° C., under nitrogen flow and with mechanical stirring, for approx. 1 hour.

The resulting polysaccharide solution is left to cool at room temperature, and a solution of 0.76 g of 4-dimethylaminopyridine in 5 mL of formamide is dropped, at the rate of 1.67 mL/min. After 15 minutes, 1.0 ml of butyric anhydride is added, and left to react for 40 minutes. The reaction mixture, which is homogenous and very viscous, is transferred to 1.2 L of 0.9% NaCl (w/v).

The solution is filtered under reduced pressure through a sintered glass filter, and then further diluted with a 0.9% NaCl solution (w/v) to the final volume of 2.5 L.

The sample is purified by tangential filtration through a filter membrane with a porosity of 10 kDa, first against 0.9% NaCl (w/v), and then exhaustively against ultra-pure water.

The polysaccharide solution is finally frozen, and the product is recovered by freeze-drying; 4.90 g of white lyophilisate is obtained.

The lyophilisate is analysed by NMR.

Degree of substitution of butyric ester (DS but.): 0.23, degree of substitution of formic ester (DSform.): 0.07.

EXAMPLE 3

Synthesis of Butyric and Formic Ester of Hyaluronic Acid Sodium Salt (BUT07004)

5.00 g of sodium hyaluronate with a molecular weight of approx. 300 kDa is solubilised in 100 mL of formamide at 95° C., under nitrogen flow and with mechanical stirring, for approx. 1 hour.

The resulting polysaccharide solution is left to cool at room temperature, and a solution of 1.26 g of 4-dimethylaminopyridine in 8 mL of formamide is dropped, at the rate of 1.67 mL/min. After 15 minutes, 1.7 mL of butyric anhydride is added and left to react for 40 minutes. The reaction mixture, which is homogenous and highly viscous, is transferred to 1.2 L of 0.9% NaCl (w/v).

The solution is filtered under reduced pressure through a sintered glass filter, and then further diluted with a 0.9% NaCl solution (w/v) to the final volume of 2.5 L.

The sample is purified by tangential filtration through a filter membrane with a porosity of 10 kDa, first against 0.9% NaCl (w/v), and then exhaustively against ultra-pure water.

The polysaccharide solution is finally frozen, and the product is recovered by freeze-drying; 4.79 g of white lyophilisate is obtained.

The lyophilisate is analysed by $^1$H NMR.

Degree of substitution of butyric ester (DS but.): 0.50, degree of substitution of formic ester (DSform.): 0.06.

EXAMPLE 4

Synthesis of Butyric and Formic Ester of Hyaluronic Acid Sodium Salt (BUT07001)

5.00 g of sodium hyaluronate with a molecular weight of approx. 300 kDa is solubilised in 100 mL of formamide at 95° C., under nitrogen flow and with mechanical stirring, for approx. 1 hour.

The resulting polysaccharide solution is left to cool at room temperature, and a solution of 1.67 g of 4-dimethylaminopyridine in 10 mL of formamide is dropped, at the rate of 1.67 mL/min. After 15 minutes, 2.25 ml of butyric anhydride is added and left to react for 40 minutes. The reaction mixture, which is homogenous and highly viscous, is transferred to 1.2 L of 0.9% NaCl (w/v).

The solution is filtered under reduced pressure through a sintered glass filter, and then further diluted with a 0.9% NaCl solution (w/v) to the final volume of 2.5 L.

The sample is then purified by tangential filtration through a filter membrane with a porosity of 10 kDa, first against 0.9% NaCl (w/v), and then exhaustively against demineralised water.

The polysaccharide solution is finally frozen, and the product is recovered by freeze-drying; 5.15 g of white lyophilisate is obtained.

The lyophilisate is analysed by $^1$H NMR.

Degree of substitution of butyric ester (DS but.): 0.69, degree of substitution of formic ester (DSform.): 0.04.

EXAMPLE 5

Synthesis of Butyric and Formic Ester of Hyaluronic Acid Sodium Salt (BUT07007)

23.00 g of sodium hyaluronate with a molecular weight of approx. 300 kDa is solubilised in 0.46 L of formamide at 95° C., under nitrogen flow and with mechanical stirring, for approx. 1 hour.

The resulting polysaccharide solution is left to cool at room temperature, and a solution of 5.47 g of 4-dimethylaminopyridine in 20 mL of formamide is dropped, at the rate of 2.0 mL/min. After 15 minutes, 7.3 ml of butyric anhydride is added and left to react for 40 minutes. The reaction mixture, which is homogenous and highly viscous, is transferred to 2.5 L of 0.9% NaCl (w/v).

The solution is filtered under reduced pressure through a sintered glass filter, and then further diluted with a 0.9% NaCl solution (w/v) to the final volume of 8.0 L.

The sample is purified by tangential filtration through a filter membrane with a porosity of 10 kDa, first against 0.9% NaCl (w/v), and then exhaustively against ultra-pure water.

The polysaccharide solution is finally frozen, and the product is recovered by freeze-drying; 22.26 g of white lyophilisate is obtained.

The lyophilisate is analysed by $^1$H NMR.

Degree of substitution of butyric ester (DS but.): 0.41, degree of substitution of formic ester (DSform.): 0.07.

EXAMPLE 6

Synthesis of Butyric and Formic Ester of Hyaluronic Acid Sodium Salt (BUT07008)

23.00 g of sodium hyaluronate with a molecular weight of approx. 300 kDa is solubilised in 0.46 L of formamide at 95° C., under nitrogen flow and with mechanical stirring, for approx. 1 hour.

The resulting polysaccharide solution is left to cool at room temperature, and a solution of 7.71 g of 4-dimethylaminopyridine in 35 mL of formamide is dropped, at the rate of 3.5 mL/min. After 15 minutes, 10.3 ml of butyric anhydride is added and left to react for 40 minutes. The reaction mixture, which is homogenous and highly viscous, is transferred to 7.0 L of 0.9% NaCl (w/v).

The solution is filtered under reduced pressure through a sintered glass filter, and then further diluted with a 0.9% NaCl solution (w/v) to the final volume of 8.0 L.

The sample is purified by tangential filtration through a filter membrane with a porosity of 10 kDa, first against 0.9% NaCl (w/v), and then exhaustively against ultra-pure water.

The polysaccharide solution is finally frozen, and the product is recovered by freeze-drying; 23.50 g of white lyophilisate is obtained.

The lyophilisate is analysed by $^1$H NMR.

Degree of substitution of butyric ester (DS but.): 0.54, degree of substitution of formic ester (DSform.): 0.10.

EXAMPLE 7

Synthesis of Sodium Salt of Butyric and Formic Ester of Hyaluronic Acid (BUT07014)

150.00 g of sodium hyaluronate with a molecular weight of approx. 300 kDa is solubilised in 3 L of formamide at 95° C., under nitrogen flow and with mechanical stirring, for 1 hour 45 minutes.

The resulting polysaccharide solution is left to cool at room temperature, and a solution of 32.00 g of 4-dimethylaminopyridine in 200 mL of formamide is dropped, at the rate of 20.0 mL/min. After 15 minutes, 43.0 ml of butyric anhydride is added, and left to react for 45 minutes. The reaction mixture, which is homogenous and highly viscous, is transferred to 4.0 L of ultra-pure water.

The solution is filtered under reduced pressure through a sintered glass filter, and then further diluted with ultra-pure water to the final volume of 30.0 L.

The sample is then purified by tangential filtration through a filter membrane with a porosity of 10 kDa, first against 0.9% NaCl (w/v), and then exhaustively against ultra-pure water.

The solution is then sterilised by passing it under pressure (2 bars) through an 0.22 μm filter membrane, and finally frozen.

The product is recovered by freeze-drying, to obtain 140 g of white lyophilisate.

The lyophilisate is analysed by $^1$H NMR.

Degree of substitution of butyric ester (DS but.): 0.32, degree of substitution of formic ester (DSform.): 0.07.

EXAMPLE 8

Synthesis of Butyric and Formic Ester of Chondroitin Sulphate Sodium Salt (BUT07015)

201.9 mg of chondroitin sulphate with a molecular weight of approx. 20 kDa is solubilised in 1 mL of formamide at 95° C., under nitrogen flow and with mechanical stirring, for approx. 20 minutes.

The resulting polysaccharide solution is left to cool to room temperature, and a solution of 49.2 mg of 4-dimethylaminopyridine in 0.5 mL of formamide is added. 65 μl of butyric anhydride is added after 15 minutes, and left to react for 40 minutes.

The product is recovered by precipitation in 20 volumes of acetone, washed 3 times with acetone and then dried at low pressure.

180.0 mg of white solid is obtained. The sample is analysed by $^1$H NMR.

Degree of substitution of butyric ester (DS but.): 0.50, degree of substitution of formic ester (DS form.): 0.03.

EXAMPLE 9

Preparation of an O/W Elasticising Cream

A non-limiting example of the invention, which illustrates the preparation of a cream formulation containing one of the butyric/formic esters according to the invention, is set out below.

The O/W cream formulation contains the compound described in example 2 as elasticising and moisturising agent, at the concentration of 0.1%, suitably mixed with common excipients used in dermatological cosmetics, such as emulsifiers, thickeners, oils, moisturisers, gelling agents, preservatives, etc.

Briefly, the process is as follows:

Approximately 600 ml of demineralised water (corresponding to approx. 60% by weight of the total formulation) is loaded into a turboemulsifier, and the pre-melted fatty phase is added under stirring at approx. 70° C. The mixture is emulsified, and cooled slowly to the temperature of 35-40° C. The thermolabile and volatile components are added at this temperature, followed by the butyric/formic ester of HA sodium salt described in example 2, dissolved in a suitable quantity of water. The mixture is left under slow stirring until the temperature of 25-30° C. is reached, and the finished product is then discharged into a suitable container.

The result is a cream with the following composition (% W/W):

| | |
|---|---|
| Butyric/formic ester of HA sodium (Example 2) | 0.1 |
| Oils (palmitic/caprylic glycerides-triglycerides) | 12 |
| Non-ionic emulsifiers | 6 |
| Cetyl alcohol | 2 |
| Dimethicone | 4 |
| MgAl silicate | 2 |
| Glycerin | 3 |
| Xylitol | 2 |
| Parabens | 0.7 |
| H₂O q.s. to 100 | |

The invention claimed is:

1. Acid polysaccharides comprising alcohol groups esterified with butyric and formic acids, wherein the polysaccharide is a glycosaminoglycan.

2. Acid polysaccharides as claimed in claim 1, wherein the glycosaminoglycan is selected from the group consisting of hyaluronic acid, chondroitin sulphate, dermatan sulphate, heparan sulphate and keratan sulphate.

3. Acid polysaccharides as claimed in claim 1, wherein the carboxyl group is present in acid form or salified with alkali metals.

4. Acid polysaccharides as claimed in claim 1, wherein the molecular weight is selected from the range of between $10^3$ and $10^7$ daltons.

5. Acid polysaccharides as claimed in claim 1, wherein the polysaccharide is hyaluronic acid with a molecular weight of between $10^4$ and $10^6$ daltons.

6. Acid polysaccharides as claimed in claim 1, wherein the degree of esterification of butyric acid on the hydroxyl groups of the polysaccharide is between 0.01 and 1*N, where N is the number of free alcohol groups present in the repetitive unit, while the degree of esterification of formic acid on the hydroxyl groups of the polysaccharide is between 0.01 and 0.20.

7. Acid polysaccharides as claimed in claim 1, wherein the degree of esterification of butyric acid on the hydroxyl groups of the polysaccharide is between 0.01 and 0.2*N, where N is the number of free alcohol groups present in the repetitive unit, while the degree of esterification of formic acid on the hydroxyl groups of the polysaccharide is between 0.01 and 0.20.

8. Acid polysaccharides as claimed in claim 7, wherein the acid polysaccharide is hyaluronic acid, and wherein the degree of esterification of butyric acid on the hydroxyl groups of the polysaccharide is between 0.01 and 0.8, while the degree of esterification of formic acid on the hydroxyl groups of the polysaccharide is between 0.01 and 0.20.

9. Acid polysaccharides of claim 1, wherein the carboxyl group is salified with sodium.

10. Process for the preparation of acid polysaccharides of claim 1, said process comprising:
   a) dissolving the acid polysaccharide, salified with sodium or other alkali metals, in formamide by heating to obtain a solution;
   b) adding butyric anhydride to the resulting solution, at room temperature, in the presence of an organic base to obtain a homogenous viscous reaction mixture;
   c) diluting the homogenous, viscous reaction mixture with an aqueous solution of NaCl and neutralising it to pH 6-7.5;
   d) purifying the dilute reaction mixture by dialysis or tangential filtration; and
   e) freezing the purified polysaccharide solution and recovering the product by freeze-drying or spray-drying.

11. Process as claimed in claim 10, wherein the organic base is an aromatic or aliphatic organic base comprising one atom of trisubstituted nitrogen.

12. Process as claimed in claim 10, wherein the solubilisation temperature of polysaccharide in formamide is between 60° C. and 120° C.

13. Process of claim 12, wherein said temperature is 95° C.

14. Process of claim 10, wherein the organic base is dimethylaminopyridine or triethylamine.

15. Process for the preparation of acid polysaccharides of claim 1, wherein the formate ester originates from hydrolysis of the formamide in the presence of butyric anhydride and a base.

16. Topical compositions containing the acid polysaccharide of claim 1, and dermatologically acceptable inert carriers.

17. Topical compositions as claimed in claim 16, including between 0.05% and 5% of polysaccharide acid by weight of the composition.

18. Topical compositions as claimed in claim 16, selected from the group consisting of creams, ointments, gels, hydrophilic liquids, aqueous or water-alcohol lotions, oil/water or water/oil emulsions.

19. A method of treatment of skin comprising applying the topical composition of claim 16 to the skin of patients in need thereof, the composition further comprising moisturizing, elasticizing, skin-toning and anti-acne agents.

20. A method for adjuvant treatment of skin lesions comprising applying the topical composition of claim 16 to patients in need thereof.

21. The method of claim 20, wherein the skin lesions are inflammations, chronic ulcers, wounds, atopic or contact dermatitis, or skin hyperthermia caused by radiation.

* * * * *